US00PP36981P2

(12) United States Plant Patent
van Eijk

(10) Patent No.: US PP36,981 P2
(45) Date of Patent: Sep. 23, 2025

(54) ***AGAPANTHUS* PLANT NAMED 'FO21WM111'**

(50) Latin Name: ***Agapanthus* hybrid**
Varietal Denomination: FO21WM111

(71) Applicant: Bianca Theodora Helena van Eijk, Nootdorp (NL)

(72) Inventor: Bianca Theodora Helena van Eijk, Nootdorp (NL)

(73) Assignee: EIJCO B.V., Nootdorp (NL)

( * ) Notice: Subject to any disclaimer, the term of this patent is extended or adjusted under 35 U.S.C. 154(b) by 0 days.

(21) Appl. No.: 18/976,959

(22) Filed: Dec. 11, 2024

(30) Foreign Application Priority Data

Sep. 23, 2024 (QZ) ..... PBR 20242221

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
CPC ..... A01H 5/02; A01H 5/00; A01H 6/04
See application file for complete search history.

(56) References Cited

PUBLICATIONS

Moany Nursery Double Diamond *Agapanthus* retrieved on Mar. 3, 2025 at https://plants.moananursery.com/12170011/Plant/Print?id=31059, 2 pp. (Year: 2025).*

* cited by examiner

*Primary Examiner* — June Hwu
(74) *Attorney, Agent, or Firm* — Penny J. Aguirre

(57) ABSTRACT

A new cultivar of *Agapanthus* plant named 'FO21WM111' that is characterized by its short leaves, its high quantity of flowers per umbel that are white in color, its floriferous habit with flowering commencing early in the season, and its relatively short pedicels.

2 Drawing Sheets

Botanical classification: *Agapanthus* hybrid.
Varietal denomination: 'FO21WM111'.

CROSS REFERENCE TO RELATED APPLICATIONS

This application claims priority to European Community Plant Variety Office (CPVO) Plant Breeder's Rights Application No. 2024/2221 filed Sep. 23, 2024 under 35 U.S.C. 119(f), the entire contents of which is incorporated by reference herein. The information for the plant breeders' rights application was received directly from the Inventor. This application is co-pending with a U.S. Plant Patent Applications filed for plants derived from the same breeding program that are entitled *Agapanthus* Plant Named 'FO21BM110' (U.S. Plant Pat. No. 36,722).

BACKGROUND OF THE INVENTION

The present invention relates to a new and distinct cultivar of *Agapanthus* of hybrid origin and will be referred to hereafter by its cultivar name, 'FO21WM111'. 'FO21WM111' represents a new perennial grown for landscape and container use.

The new cultivar was derived from a controlled breeding program by the Inventor in Pijnacker, Netherlands. The goal of the breeding program was to develop new cultivars of *Agapanthus* with a high production of flowering stems on short pedicels, short plant habits, and unique flowers. The Inventor collected seeds after open pollination in July of 2016 of unnamed and unpatented proprietary plants of *Agapanthus* from the Inventors' breeding program. The collected seeds were pooled before planting and therefore the exact parents are unknown. The Inventor selected 'FO21WM111' in June of 2017 as a single unique plant amongst the seedlings that resulted seedlings.

Asexual propagation of the new cultivar was first accomplished by division by the Inventor in Pijnacker, Netherlands in July of 2018. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'FO21WM111' as a distinct cultivar of *Agapanthus*.

1. 'FO21WM111' exhibits short leaves.
2. 'FO21WM111' exhibits a high quantity of flowers per umbel that are white in color.
3. 'FO21WM111' exhibits a floriferous habit with flowering commencing early in the season.
4. 'FO21WM111' exhibits relatively short pedicels.

'FO21WM111' can be most closely compared to the *Agapanthus* cultivars 'RFDD' (not patented), 'Verag W01' (not patented), and 'FO21BM110'. 'RFDD' is similar to 'FO21WM111' in having white flowers. 'RFDD' differs from 'FO21WM111' in having longer pedicels, a shorter plant height, less dense inflorescences, and double flowers. 'Verag W01' is similar to 'FO21WM111' in having white flowers and short pedicels. 'Verag W01' differs from 'FO21WM111' in having leaves that are more narrow and flower buds that are green-white in color.

'FO21BM110' is similar to 'FO21WM111' in having short leaves, relatively short pedicels and dense flowerheads. 'FO21WM111' differs from 'FO21BM110' in having violet-blue flowers and in commencing bloom later in the season.

BRIEF DESCRIPTION OF THE DRAWINGS

The accompanying color photographs illustrate the overall appearance and distinct characteristics of the new *Agapanthus*. The photographs were taken of a plant 2 years in age as grown outdoors in a 25-cm container in Nootdorp, Netherlands.

The photograph in FIG. 1 provides a side view of a plant of 'FO21WM111' in bloom.

Figure 1:
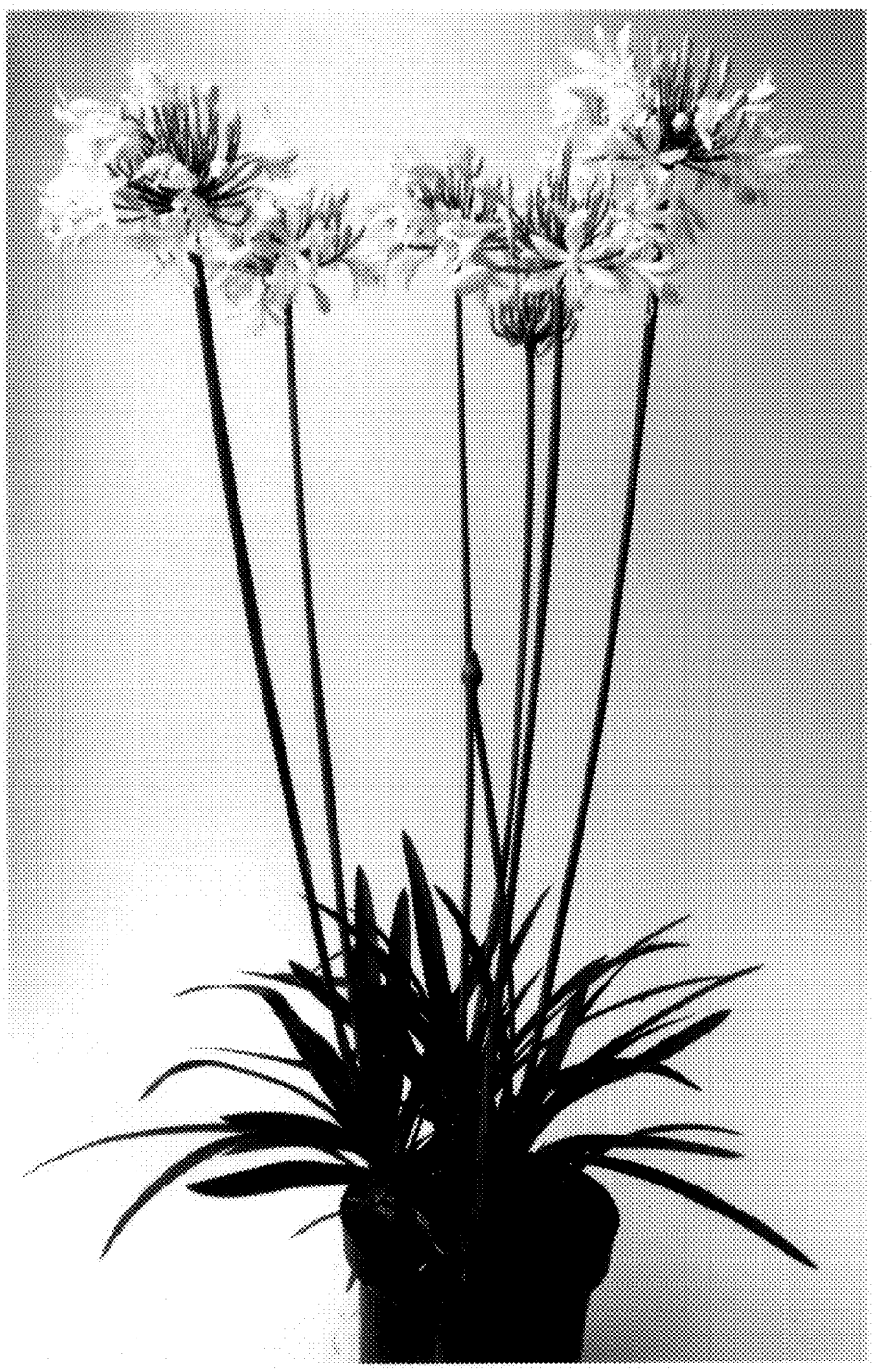
Figure 2:
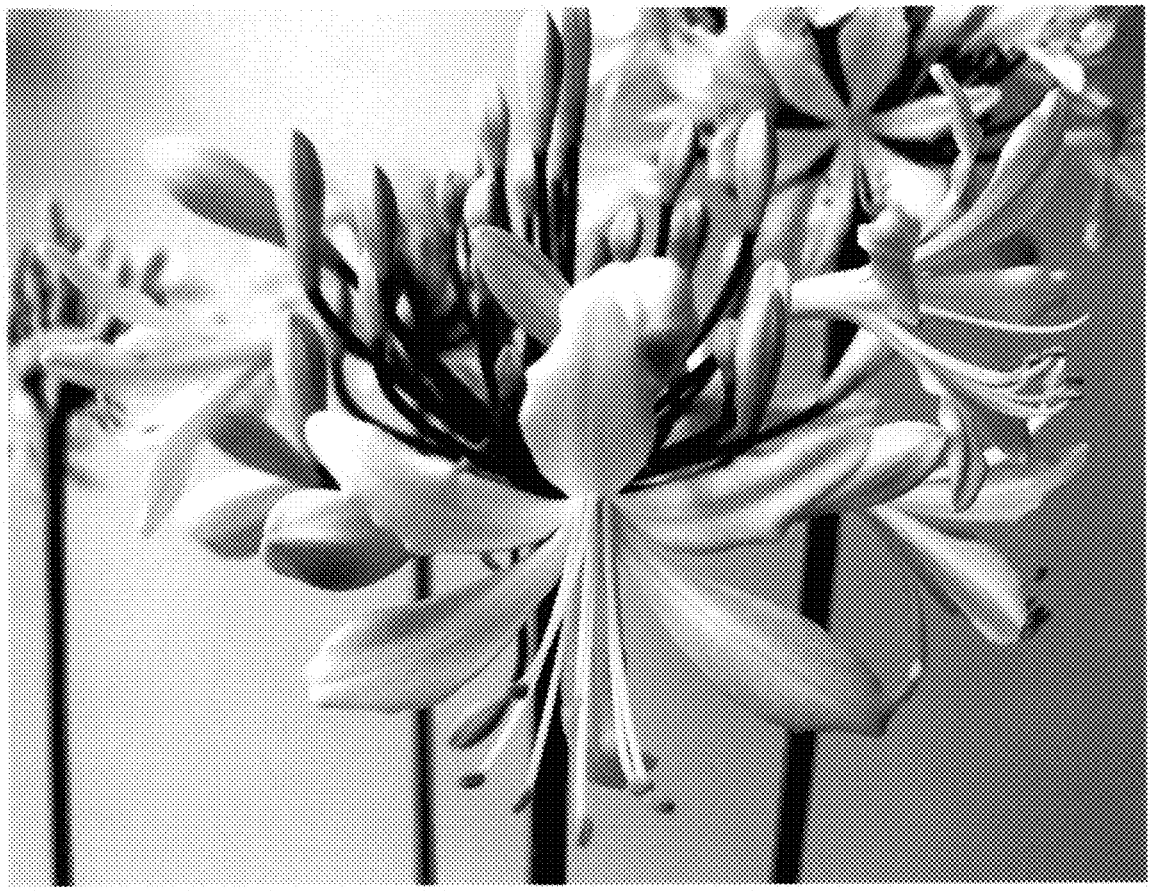

The photograph in FIG. 2 provides a close-up view of the flower and inflorescence of 'FO21WM111'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 2-year-old plants of 'FO21WM111' as grown outdoors in 25-cm containers in Nootdorp, Netherlands. The phenotype of the new cultivar may vary with variations in environmental, climatic, and cultural conditions, as it has not been tested under all possible environmental conditions. The color determinations are in accordance with The 2015 Colour Chart of The Royal Horticultural Society (2019 reprint), London, England, except where general color terms of ordinary dictionary significance are used.

General description:

*Blooming period*.—May through November in The Netherlands (climate dependent).

*Plant type*.—Semi-deciduous (climate dependent) herbaceous perennial.

*Plant habit*.—Basal rosettes with inflorescences emerging from the rosette center.

*Height and spread*.—An average of 18 cm in height from soil to top of foliar plane and 46 cm in height from soil level to top of floral plane and 52 cm in diameter as a 2-year-old plant grown in a container.

*Cold hardiness*.—At least to U.S.D.A. Zone 8.

*Diseases and pests*.—No resistance or susceptibility to diseases or pests has been observed.

*Root description*.—Thick and fleshy.

*Propagation*.—Division and Tissue culture (preferred).

*Time required for root development*.—Time for root initiation; 6 weeks from tissue culture and 3 to 8 weeks from division, time to produce a rooted cutting; 6 to 10 months to produce a young plant from a tissue culture plug or division.

*Growth rate*.—Moderately vigorous.

*Number of rosettes*.—An average of 7 rosettes per 25-cm container as a 2-year-old plant.

Foliage description:

*Leaf shape*.—Ligulate

*Leaf division*.—Simple.

*Leaf base*.—Decurrent, broadly cuneate.

*Leaf arrangement*.—In basal rosettes, equitant.

*Leaf apex*.—Acute.

*Leaf aspect*.—Moderately carinate, slightly to moderately curved.

*Leaf venation*.—Parallel, upper surface NN137A and lower surface NN137B.

*Leaf margins*.—Entire.

*Leaf size*.—Average of 26.6 cm in length, 2.1 cm in width.

*Leaf surface*.—Smooth, glabrous, and dull on upper and lower surface.

*Leaf number*.—Average of 14 leaves per rosette.

*Density of the foliage*.—Medium.

*Leaf color*.—Young leaves upper surface; 137B, young leaves lower surface; 138B, mature leaves upper surface; NN137B, veins NN137A, mature leaves lower surface; 137C, veins NN137B, anthocyanin at base at leaf; absent.

*Leaf attachment*.—Sessile to base.

Flower description:

*Inflorescence type*.—Umbel.

*Flower fragrance*.—None.

*Flower type*.—Campanulate with 23% fused at the base.

*Flower number*.—An average of 50 flowers and flower buds per umbel, flowers and buds per plant 350.

*Inflorescence size*.—Average of 9 cm in height, 13.7 cm in diameter.

*Flower size*.—An average of 4.5 cm in depth and diameter, throat is 4 mm in diameter, tube is 1.1 cm in length, 6 mm in diameter.

*Lastingness of inflorescence*.—Average of 2 weeks, self-cleaning.

*Flower aspect*.—Outwardly to upright.

*Peduncle*.—1 per rosette, strong, oval in shape, held primarily upright, surface is glabrous and smooth, moderately glossy, covered with a very thin waxy layer 193D in color, average of 38.1 cm in length and 8 mm in width at the widest point, 5 mm at the narrowest point, 144A in color, anthocyanin absent.

*Pedicels*.—Strong, average of 3.2 cm in length and 1.5 mm in width, held erect to outward, 143A in color, smooth and glabrous surface.

*Flower buds*.—Oblanceolate in shape, smooth, slightly velvety, matte surface, average of 2.5 cm in length and 6 mm in width, 155C in color.

*Tepals*.—6, 2 whorls, oblanceolate in shape, fused, entire margins, lower tepals acute, upper tepals bluntly acute, both surfaces are glabrous, slightly velvety, 4.7 cm in length, lower tepal 8.5 mm in width, upper tepal 1.2 cm in width, color when opening and fully open upper and lower surface NN155D with longitudinal central stripe NN155B.

*Bracts*.—Immature inflorescence covered with 2 bracts, placed oppositely and dropped when individual flowers develop to open, broadly ovate in shape, average of 3.1 cm in length, 1.6 cm in width, color; upper side 145C, veins 145A, lower surface 144C, at the base of each individual pedicel, a single bract is present, filiform in shape, average of 1.5 cm in length and 1 mm in width, color; 158D, main vein 164B, anthocyanin absent.

Reproductive organs:

*Gynoecium*.—Pistil; 1, average of 3.3 cm in length, stigma; club-shaped, 1 mm in length, 5 mm in diameter, NN155D in color, style; 3.2 cm in length, NN155D, ovary; 154D in color.

*Androecium*.—Stamens; 6, extrusion weak, anthers; basifixed, oblong in shape, average of 5 mm in length, 1.5 mm in width, 151D in color, filament; 3.5 cm in length, and NN155D in color, pollen; moderate in quantity and 7A in color.

*Fruit/seed*.—None observed to date.

It is claimed:

1. A new and distinct cultivar of *Agapanthus* plant named 'FO21WM111' as herein illustrated and described.

* * * * *